(12) United States Patent
Wulfman et al.

(10) Patent No.: US 9,272,135 B2
(45) Date of Patent: Mar. 1, 2016

(54) CABLE CONDUCTOR FITTING

(71) Applicant: Cardiac Pacemakers, Inc., St. Paul, MN (US)

(72) Inventors: David R. Wulfman, Minneapolis, MN (US); Michael A. Felling, Osceola, WI (US); Benjamin J. Haasl, Forest Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/714,537

(22) Filed: May 18, 2015

(65) Prior Publication Data

US 2015/0246224 A1    Sep. 3, 2015

Related U.S. Application Data

(62) Division of application No. 14/154,386, filed on Jan. 14, 2014, now Pat. No. 9,037,260.

(60) Provisional application No. 61/752,782, filed on Jan. 15, 2013.

(51) Int. Cl.
| *A61N 1/05* | (2006.01) |
| *A61N 1/375* | (2006.01) |
| *B23K 20/00* | (2006.01) |
| *B23K 31/02* | (2006.01) |

(52) U.S. Cl.
CPC ............... *A61N 1/0587* (2013.01); *A61N 1/05* (2013.01); *A61N 1/056* (2013.01); *A61N 1/0563* (2013.01); *A61N 1/375* (2013.01); *B23K 20/002* (2013.01); *B23K 31/02* (2013.01); *Y10T 29/49208* (2015.01); *Y10T 29/49213* (2015.01)

(58) Field of Classification Search
CPC ......... A61N 1/05; A61N 1/0563; A61N 1/36; A61N 1/39; A61N 1/3956; A61N 1/04
USPC ............................................. 607/115–116, 5
See application file for complete search history.

(56) References Cited

U.S. PATENT DOCUMENTS

| 5,014,720 A | 5/1991 | Barcel et al. |
| 5,522,872 A | 6/1996 | Hoff |

(Continued)

OTHER PUBLICATIONS

International Search Report and Written Opinion issued in PCT/US2014/011406, mailed May 6, 2014, 8 pages.

(Continued)

*Primary Examiner* — Paula J Stice
(74) *Attorney, Agent, or Firm* — Faegre Baker Daniels LLP

(57) ABSTRACT

Various embodiments concern a lead comprising a cable conductor and a coil electrode having one or more filars, the one or more filars wound in a helical pattern. The lead can further include an inner fitting axially aligned with the coil electrode. The inner fitting can comprise external threading and a slot extending along the inner fitting. The slot can receive a portion of the cable conductor. The lead can include an outer tubular fitting having a lumen with internal threading. Each of the coil electrode and the inner fitting can be partially received within the lumen, both of the external threading and the one or more filars threadedly engaged with the internal threading. The cable conductor can be pinched in the slot to mechanically connect the cable conductor to the inner fitting. The pinching can be supported by the outer tubular fitting.

20 Claims, 6 Drawing Sheets

(56) References Cited

U.S. PATENT DOCUMENTS

| | | |
|---|---|---|
| 6,456,888 B1 | 9/2002 | Skinner et al. |
| 2009/0281607 A1 | 11/2009 | Arnholt |
| 2010/0249892 A1 | 9/2010 | Bulkes et al. |
| 2010/0305670 A1 | 12/2010 | Hall et al. |
| 2011/0079423 A1 | 4/2011 | Zhao et al. |
| 2011/0245887 A1 | 10/2011 | Klardie et al. |
| 2011/0282420 A1 | 11/2011 | Seifert et al. |

OTHER PUBLICATIONS

International Search Report and Written Opinion issued in PCT/US2014/011479, mailed Apr. 10, 2014, 9 pages.

CABLE CONDUCTOR FITTING

CROSS-REFERENCE TO RELATED APPLICATION

This application is a division of U.S. Pat. No. 9,037,260, filed Jan. 14, 2014, which claims priority to U.S. Provisional Application 61/752,782, filed Jan. 15, 2013, which is herein incorporated by reference in its entirety.

TECHNICAL FIELD

The present disclosure relates generally to implantable leads. More specifically, the present disclosure relates to connecting of a cable conductor within an implantable lead.

BACKGROUND

When functioning properly, the human heart maintains its own intrinsic rhythm and is capable of pumping adequate blood throughout the body's circulatory system. However, some individuals have irregular cardiac rhythms, referred to as fibrillation or arrhythmias, which can result in improper cardiac rhythms. One manner of treating improper cardiac rhythms include the use of a pulse generator (PG) such as a pacemaker, an implantable cardioverter defibrillator (ICD), or a cardiac resynchronization (CRT) device. Such devices are typically coupled to one or more implantable leads having one or more elements that can be used to deliver electrical energy to the heart. Implantable leads can additionally or alternatively be used to stimulate other tissues of the body, such as nervous and/or musculature systems.

SUMMARY

Example 1 concerns an implantable lead comprising: a lead body having a proximal end and a distal end; a cable conductor extending within the lead body; a coil electrode having one or more filars, the coil electrode extending along a portion of the distal end of the lead body, the one or more filars wound in a helical pattern; an inner fitting axially aligned with the coil electrode, at least a portion of the inner fitting comprising external threading, the inner fitting having a slot extending along the inner fitting, the slot receiving at least a portion of the cable conductor; and an outer tubular fitting having a lumen with internal threading, each of the coil electrode and the inner fitting at least partially received within the lumen, both of the external threading and the one or more filars threadedly engaged with the internal threading, the cable conductor pinched in the slot to mechanically connect the cable conductor to the inner fitting, the pinching of the cable conductor supported by reception of the inner fitting within the lumen of the outer tubular fitting.

In example 2, the implantable lead of example 1, wherein the slot has a floor and the cable conductor is pinched by direct contact with each of the floor and the internal threading.

In example 3, the implantable lead of either of examples 1 and 2, wherein the inner fitting is an inner tubular fitting having a wall and the slot is defined by the wall.

In example 4, the implantable lead of example 3, wherein the slot is an indentation in the wall.

In example 5, the implantable lead of example 3, wherein the slot is a gap defined by two opposing sides of the wall, and the cable conductor is pinched by the two opposing sides of the wall.

In example 6, the implantable lead of any of examples 1-5, wherein the slot is relatively wider to receive the cable conductor when the inner fitting is outside of the lumen and the slot is relatively narrower to pinch the cable conductor when the inner fitting is received within the lumen.

In example 7, the implantable lead of any of examples 1-6, wherein the helical pattern of the one or more filars and the external threading are aligned to form a continuous thread pattern that overlaps each of the inner fitting and the coil electrode, and the internal threading is threadedly engaged with the continuous thread pattern along each of the inner fitting and the coil electrode.

In example 8, the implantable lead of any of examples 1-7, wherein the coil electrode is welded directly to the inner tubular fitting.

In example 9, wherein the one or more filars comprises a plurality of filars arranged in a grouping of adjacent filars that spirals in the helical pattern, a space exists between each turn of the grouping, and the internal threading projects into the space.

In example 10, the implantable lead of any of examples 1-9, wherein the outer tubular fitting defines at least part of an exterior surface of the implantable lead.

In example 11, the implantable lead of any of examples 1-10, wherein each of the inner fitting and the outer tubular fitting are formed from electrically conductive material, and one or both of the inner fitting and the outer tubular fitting electrically connect the cable conductor to the coil electrode.

In example 12, the implantable lead of any of examples 1-11, further comprising a polymer sleeve having a wall, the polymer sleeve extending over the coil electrode, the wall of the polymer sleeve configured to allow the delivery of the defibrillation therapy through the wall, wherein the polymer sleeve extends into the lumen and the wall of the polymer sleeve is compressed between the internal threading and the one or more filars to mechanically connect the polymer sleeve to the outer tubular fitting.

In example 13, the implantable lead of any of examples 1-12, wherein the slot of the tubular fitting curves along a longitudinal axis of the tubular fitting.

Example 14 concerns a method for assembling an implantable lead, the method comprising: placing a cable conductor within a slot of an inner fitting, the inner fitting comprising external threading that extends over at least a portion of the inner fitting; axially aligning a coil electrode with the inner fitting, the coil electrode having one or more filars, the one or more filars wound in a helical pattern; and inserting the coil electrode and the inner fitting into a lumen of an outer tubular sleeve, the lumen having internal threading, wherein one or more of the outer tubular fitting, the coil electrode, and the inner fitting are rotated during the insertion such that the internal threading threadably engages both of the one or more filars and the external threading, the cable conductor is pinched within the slot as the inner fitting is inserted into the lumen, and the pinching mechanically connects the cable conductor to the inner fitting.

In example 15, the method of example 14, wherein axially aligning the coil electrode with the inner fitting comprises aligning the helical pattern of the one or more filars with the external threading to form a continuous thread pattern that overlaps each of the inner fitting and the coil electrode.

In example 16, the method of either of examples 14 or 15, wherein the slot is a gap in a wall of the inner fitting and the insertion of the inner fitting into the lumen narrows the gap to pinch the cable conductor.

In example 17, the method of any of examples 14-16, further comprising welding the inner fitting to the outer tubular fitting when the coil electrode is axially aligned with the inner fitting.

In example 18, the method of any of examples 14-17, wherein a layer of insulation covers the cable conductor when the cable conductor is placed within the slot, and a portion of the insulation is removed as the inner fitting is inserted into the lumen of the outer tubular sleeve.

In example 19, the method of example 18, wherein the portion of the insulation is stripped by the internal threading.

Example 20 concerns an implantable lead comprising: a lead body having a proximal end and a distal end; a cable conductor extending within the lead body; a coil electrode having one or more filars, the coil electrode extending along a portion of the distal end of the lead body; an inner fitting axially aligned with the coil electrode, at least a portion of the inner fitting comprising external threading, the inner fitting having a slot extending along the inner fitting, the slot receiving at least a portion of the cable conductor; and an outer tubular fitting having a lumen with internal threading, the inner fitting at least partially received within the lumen, the external threading threadedly engaged with the internal threading, the cable conductor pinched in the slot to mechanically hold the cable conductor and electrically connect the cable conductor to the coil electrode, the pinching of the cable conductor supported by reception of the inner fitting within the lumen of the outer tubular fitting.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

Figure 1:
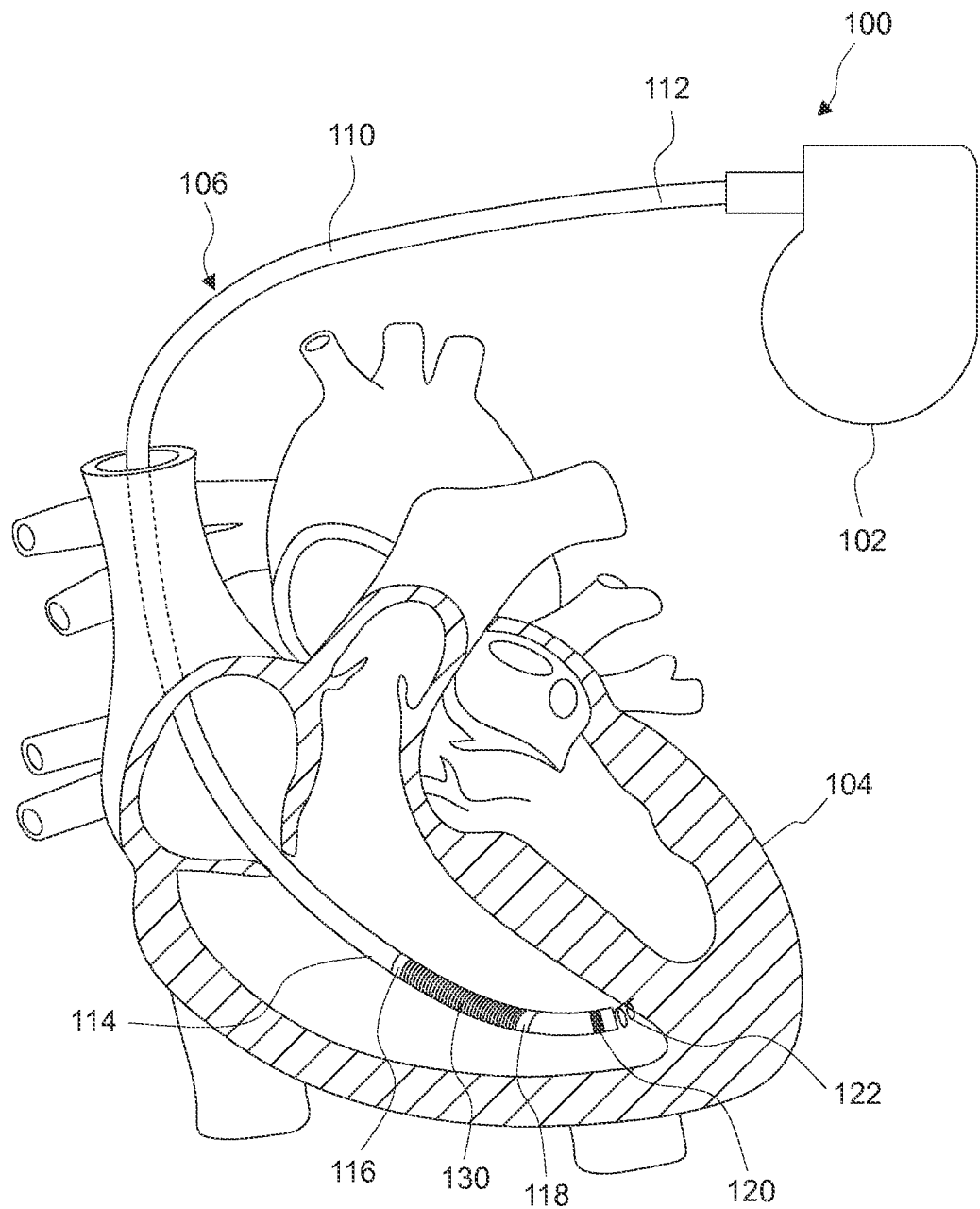
FIG. 1 is a schematic view of a cardiac rhythm management system.

While the disclosure is amenable to various modifications and alternative forms; specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

DETAILED DESCRIPTION

FIG. 1 illustrates a schematic view of a cardiac rhythm management (CRM) system 100. The CRM system can include a pulse generator 102 for delivering electrical stimulation to the heart 104. The pulse generator 102 can be implanted subcutaneously within an implantation location or pocket in the patient's chest or abdomen. The pulse generator 102 can be connected to an implantable lead 106. The implantable lead 106 can conduct electrical signals between the pulse generator 102 and the heart 104 or other tissue. The implantable lead 106 can include a lead body 110, a proximal end 112, and a distal end 114. The proximal end 112 of the implantable lead 106 can mechanically and electrically connect with the pulse generator 102. In various embodiments, the implantable lead 106 can enter the vascular system through a vascular entry site formed in the wall of the left subclavian vein or other location. The implantable lead 106 can extend through the left brachiocephalic vein and the superior vena cava such that the distal end 114 of the implantable lead 106 can be implanted in the right atrium, right ventricle, left ventricle, or other location.

The distal end 114 of the implantable lead 106 can include one or more electrodes for sensing bioelectrical signals and/or delivering electrical energy to the heart 104. For example, the distal end 114 of the implantable lead 106 can include a ring electrode 120. The distal end 114 of the implantable lead 106 can include a fixation element 122 which, in addition to anchoring the distal end 114 to tissue, can be configured to sense bioelectrical signals and/or deliver electrical energy. The distal end 114 can include a coil electrode 130, which is further discussed herein. While one coil electrode 130 is illustrated in FIG. 1, various embodiments of the implantable lead 106 may include a plurality of coil electrodes, such as two or more coil electrodes.

The coil electrode 130 can extend along a portion of the distal end 114 of the lead body 110. In some embodiments, the coil electrode 130 can be exposed, as shown in FIG. 1. In some embodiments, the coil electrode 130 can be partially or fully covered by a polymer sleeve, as further discussed herein. A conductor can extend within the lead body 106 to electrically connect the pulse generator 102 and the coil electrode 130 to allow the pulse generator 102 to deliver electrical energy to the heart 104 from the coil electrode 130. The coil electrode 130 can be configured to sense bioelectrical signals and/or deliver electrical energy. In some embodiments, the coil electrode 130 can be used to deliver a defibrillation therapy comprising a high voltage signal that depolarizes a critical mass of the cardiac tissue to terminate an arrhythmia and allow a normal sinus rhythm to be reestablished. While use of the coil electrode 130 for delivering a defibrillation therapy to the heart 104 is mainly discussed herein, the coil electrode 130 can be used for delivering other therapies to the heart 104 or other tissues of the body.

The coil electrode 130 can be mechanically and electrically connected to the lead 110 by one or both of a proximal coupling 116 and a distal coupling 118, as further discussed herein. As shown in FIG. 1, the proximal coupling 116 can be proximal of the coil electrode 130. The distal coupling 118 can be distal of the coil electrode 130. In some embodiments, only one of the proximal and distal couplings 116, 118 may be provided on the lead body 110.

Figure 2:
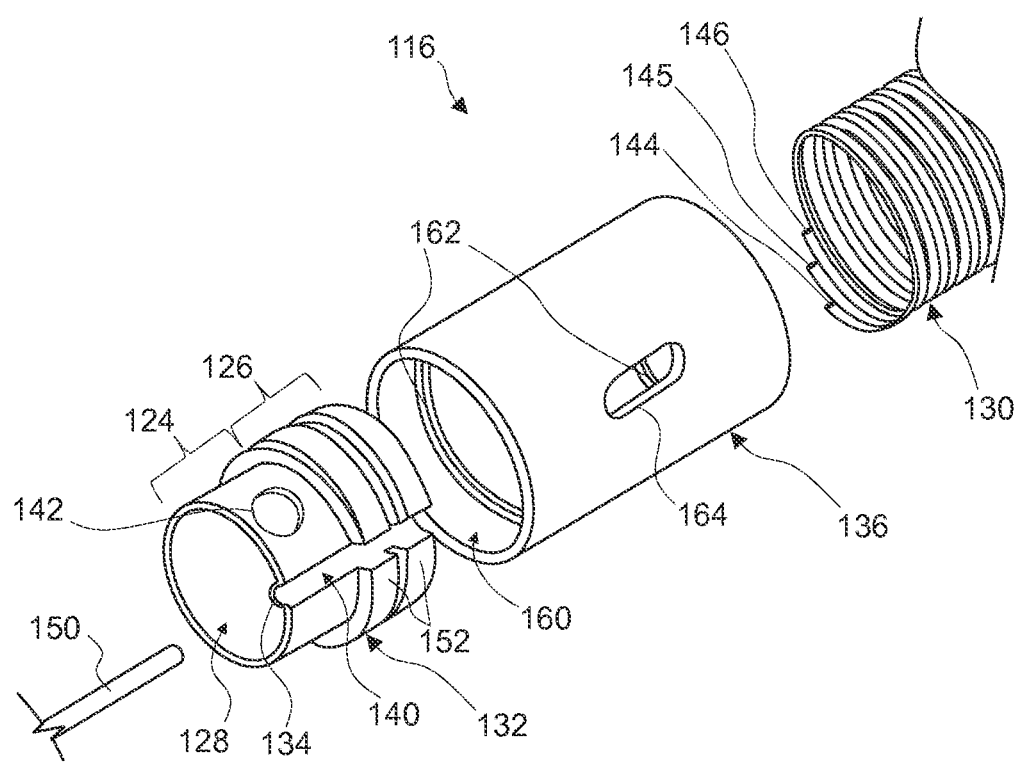
FIG. 2 is an exploded view of a coupling for connecting a cable conductor and a coil electrode.

FIG. 2 illustrates an exploded view of the proximal coupling 116. The proximal coupling 116 can include an outer tubular fitting 136 and an inner fitting 132. The outer tubular fitting 136 and the inner fitting 132 can mechanically and electrically connect the coil electrode 130 to the cable conductor 150 to allow electrical energy to be delivered from the coil electrode 130 to tissue. As will be further described herein, the cable conductor 150 can be pinched when the inner fitting 132 is received within the lumen 160 of the outer fitting 136. The pinching of the cable conductor 150 can anchor the cable conductor 150 to the each of the outer tubular fitting 136 and the inner fitting 132 to maintain the electrical connection with the coil electrode 130.

The cable conductor 150 can be formed from metal material. In some embodiments, the cable conductor 150 can be formed from one or more wires. The cable conductor 150 can extend to the proximal end 112 of the implantable lead 106.

The cable conductor 150 can electrically connect with one or more channels of the pulse generator 102 for conducting electrical energy along the lead body 110.

The inner fitting 132 can be a tubular body. The inner fitting 132 can have a lumen 128 that extends the full length of the inner fitting 132. The inner fitting 132 can have a first portion 124 and a second portion 126. External threading 152 can extend along the second portion 126. The first portion 124 can be a longitudinal section of the inner fitting 132 that has no external threading. In some embodiments, the external threading 152 can extend along the entire length of the inner fitting 132. The first portion 124 can have an outer diameter that is smaller than an outer diameter of the second portion 126. In some embodiments, the larger diameter of the second portion 126 can be attributable to the presence of the external threading 152 along the second portion 126. The inner fitting 132 may be formed from metal, such as platinum or titanium. The inner fitting 132 can be formed by, for example, one or more of casting, extrusion, stamping, and/or machining processes.

The inner fitting 132 can include a slot 140. The slot 140 can extend longitudinally along the exterior of the inner fitting 132. In some embodiments, the slot 140 can be formed from an indentation in the wall of the inner fitting 132. The indentation can form a corresponding bulge within the lumen 128 of the inner fitting 132. In some embodiments, the slot 140 can be formed by removal of material from the wall of the inner fitting 132. The slot 140 can have a floor 134. The floor 134 can have a rounded or squared shape, among other configurations. In some embodiments, the slot 140 may not include a floor 134, in which case the slot 140 can be formed by a gap in the wall of the inner fitting 132, as will be further described herein.

As shown in FIG. 2, the slot 140 can extend along the entire length of the inner fitting 132 (e.g., along both of the first portion 124 and the second portion 126). In some embodiments, the slot 140 may only extend along either of the first portion 124 or the second portion 126. The slot 140 can extend parallel with a longitudinal axis of the inner fitting 132. As shown in FIG. 2, the slot 140 can be straight. In some other embodiments, the slot 140 can be curved.

The slot 140 can have a depth. The depth of the slot 140 can be measured as the radial distance between the floor 134 and the circumference of the inner fitting 132 along the slot 140. The depth of the slot 140 can be different along different portions of the inner fitting 132. For example, the slot 140 can be shallower along the first portion 124 and deeper along the second portion 126. The greater depth of the slot 140 along the second portion 126 can be due to the external threading 152. As shown in FIG. 2, the slot 140 can intersect with the external threading 152 such that the external threading 152 can include one or more discontinuities at one or more intersections with the slot 140.

The slot 140 can be dimensioned to receive at least a portion of the cable conductor 150. In some embodiments, the depth of the slot 140 can be greater than the diameter of the cable conductor 150, such that the entire circumference of the cable conductor 150 can fit within the slot 140 without protruding beyond the outer diameter of the inner fitting 132 along the slot 140. In some embodiments, the depth of the slot 140 can be less than the diameter of the slot 140, such that the cable conductor 150 extends out of the slot 140 when the cable conductor is placed along the floor 134.

The inner fitting 132 can include one or more attachment features along the first portion 124. As shown in FIG. 2, a hole 142 in the wall of the inner fitting 132 can be provided as an attachment feature for connecting the inner fitting 132 to other components of the implantable lead 106 through polymer integration, as further discussed herein.

The outer tubular fitting 136 of the coupling 116 can define an exterior surface of the implantable lead 106. The outer tubular fitting 136 can have a lumen 160. The lumen 160 can extend entirely through the outer tubular fitting 136 to have openings on each side of the outer tubular fitting 136. The outer tubular fitting 136 and the inner fitting 132 can be dimensioned such that the inner fitting 132 can be received within the lumen 160 of the outer tubular fitting 136. The outer tubular fitting 136 may be formed from metal, such as platinum or titanium. The outer tubular fitting 136 can be formed by one or more of casting, extrusion, stamping, and/or machining processes.

The lumen 160 of the outer tubular fitting 136 can include internal threading 162. The internal threading 162 can be formed by one or more spiraling features projecting inward from an inner surface of the lumen 160. The internal threading 162 can have a pitch. The internal threading 162 can have the same pitch as the external threading 152 of the inner fitting 132. In some embodiments, the pitch of the external threading 152 can be measured based on the longitudinal distance along the inner fitting 132 in which an external thread completes a full spiral (e.g., a 360 degree rotation). Likewise, the pitch of the internal threading 162 can be measured based on the longitudinal distance along the outer tubular fitting 136 in which an internal thread completes a full spiral. In some embodiments, the pitch of the external threading 152 and the internal threading 162 can be measured based on the longitudinal distance between each adjacent thread. In some embodiments, the pitch of the external threading 152 and the internal threading 162 can be measured based on the number of threads per unit distance (e.g., threads-per-inch).

The internal threading 162 can be complementary to the external threading 152 such that the internal threads 162 can receive the external threads 152 by rotation. Engagement between the internal threading 162 and the external threading 152 can mechanically connect the inner fitting 132 to the outer tubular fitting 136. The inner fitting 132 can additionally or alternatively be mechanically connected to the outer tubular fitting 136 by welding. For example, the outer tubular fitting 136 can include a window 164. The window 164 can allow welding of the inner fitting 132 to the outer tubular fitting 136 within the lumen 160 while the inner fitting 132 is received within the lumen 160.

FIG. 2 further illustrates an end of the coil electrode 130 (e.g., a proximal end of the coil electrode 130). The coil electrode 130 can be formed from one or more filars. The particular embodiment of the coil electrode 130 shown in FIG. 2 is formed from three filars 144-146, although other embodiments can have a greater or lesser number of filars. The filars 144-146 can be wound in a helical pattern. For example, the coil electrode 130 can be formed by wrapping the filars 144-146 around a mandrel in a helical pattern. The wrapping of the filars 144-146 around the mandrel can plastically deform the filars 144-146 such that the filars 144-146 are biased to retain the helical pattern. In some cases, the filars 144-146 can be thermally treated to facilitate the retention of the helical pattern. The filars 144-146 can be formed from electrically conductive material, such as platinum or titanium. The coil electrode 130 and the outer tubular fitting 136 can be dimensioned such that the coil electrode 130 can be received within the lumen 160 of the outer tubular fitting 136. For example, the outer diameter of the coil electrode 130 may be slightly smaller than the inner diameter of the lumen 160.

The helical pattern of the filars 144-146 can have a pitch. The pitch of the filars 144-146 can be similar to the pitch of either or both of the external threading 152 and the internal threading 162. In some embodiments, the pitch can be measured by the distance between each adjacent filar turn (e.g., the longitudinal distance along the coil electrode 130 between filar 144 and filar 145). In some embodiments, the pitch can be measured based on the longitudinal distance along the coil electrode 130 in which a particular filar completes one full spiral (e.g., a 360 degree rotation of filar 144). In some embodiments, the pitch can be measured based on the longitudinal distance along the coil electrode 130 between adjacent spaces 168 (shown in FIG. 3). In some embodiments, the pitch can be measured based on the number of filar turns per unit distance (e.g., filars-per-inch).

The helical pattern of the filars 144-146 can form a helical contour pattern along the exterior of the coil electrode 130. The helical contour pattern of the coil electrode 130 can be complementary to the internal threading 162. For example, an end (e.g., a proximal end) of the coil electrode 130 can be rotateably advanced into the lumen 160 to interlock the filars 144-146 and the internal threading 162 as the end of the coil electrode 130 is received within the lumen 160.

The outer diameter of the coil electrode 130 can be about the same as the outer diameter of the second portion 126 of the inner fitting 132. Similarity between the outer diameters of the coil electrode 130 and the inner fitting 132 as well as correspondence between the pitches of the helical contour pattern of the coil electrode 130 and the external threading 152 of the inner fitting 132 can allow the coil electrode 130 and the inner fitting 132 to form a continuous thread pattern that extends over each of the coil electrode 130 and the inner fitting 132 when axially aligned. For example, each of the coil electrode 130 and the inner fitting 132 can be at least partially received within the lumen 160 of the outer tubular fitting 136 at the same time. Furthermore, both of the external threading 152 of the inner fitting 132 and the helical pattern of the filars 144-146 can engage with the internal threading 162 of the outer tubular fitting 136 at the same time.

In some embodiments, the coil electrode 130 can be mechanically attached to the inner fitting 132 prior to being received within the lumen 160 of the outer tubular fitting 136. For example, an end of the coil electrode 130 (e.g., a proximal end) can be brought into contact with an end of the inner fitting 132 (e.g., a distal end) while the coil electrode 130 and the inner fitting 132 are in axial alignment. The coil electrode 130 can then be welded to the inner fitting 132. The welding can provide an electrical connection between the coil electrode 130 and the inner fitting 132. Alternative techniques for mechanically coupling the coil electrode 130 and the inner fitting 132 can be performed. After the coil electrode 130 is mechanically connected to the inner fitting 132, the assembly of the coil electrode 130 and the inner fitting 132 can be moved through the lumen 160 by rotation until the internal threading 162 engages both of the external threading 152 and the helical contour pattern of the coil electrode 130.

Figure 3:
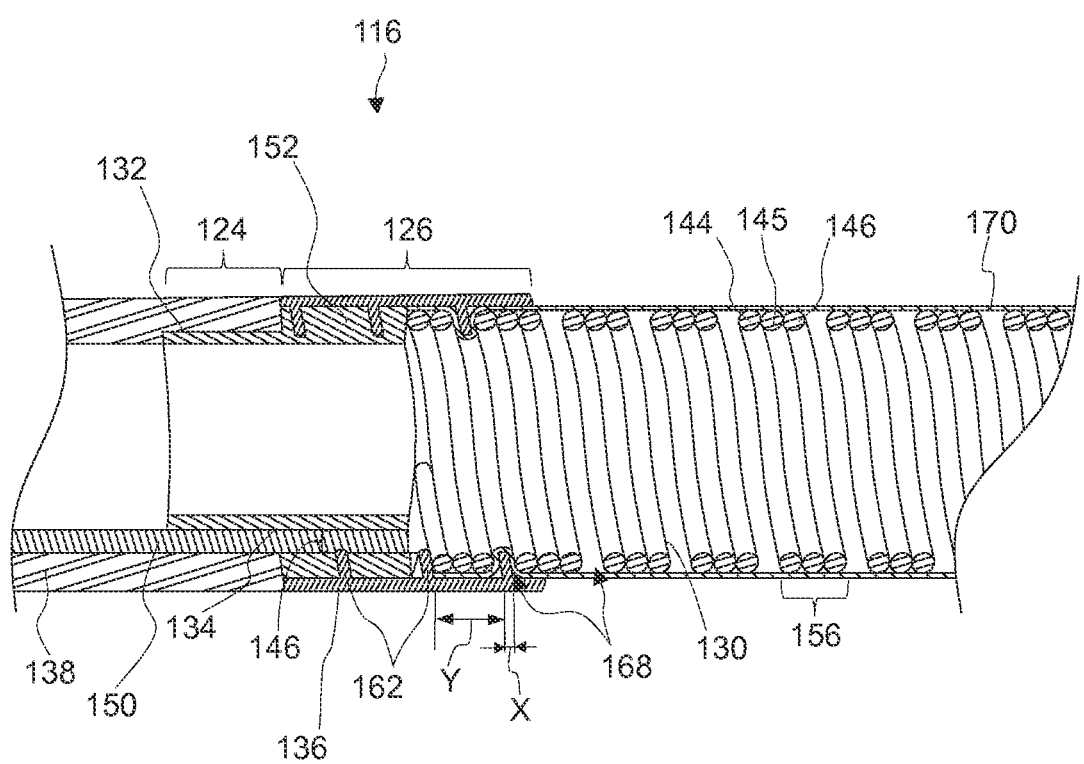
FIG. 3 is a cross-sectional view of a coupling connecting a cable conductor and a coil electrode.

FIG. 3 shows a cross sectional diagram of the coupling 116 in an assembled configuration. As shown in FIG. 3, the coil electrode 130 and the inner fitting 132 can be received within the outer tubular fitting 136 such that the outer tubular fitting 136 can overlap at least part of each of the coil electrode 130 and the inner fitting 132. FIG. 3 additionally shows that the internal threading 162 can threadedly engage with the external threading 152 of the inner fitting 132 and the helical contour pattern of the coil electrode 130. As shown in FIG. 3, the cable conductor 150 may not be in direct contact with the coil electrode 130, however each of the cable conductor 150 and the coil electrode 130 can be in contact with one or both of the inner fitting 132 and the outer tubular fitting 136 to conduct electrical energy from the cable conductor 150 to the coil electrode 130. In various other embodiments, the cable conductor 150 can be in direct contact with the coil electrode 130 to facilitate an electrical connection between the cable conductor 150 and the coil electrode 130.

As shown in FIG. 3, the filars 144-146 can form a filar grouping 156. A filar grouping can include a set of separate filars that are adjacent to one another and spiral together in a helical pattern. Space 168 can exist between the filars of adjacent turns of the grouping 156. As shown in FIG. 3, the internal threading 162 can penetrate the spaces 168 between the turns of the grouping 156. Such interaction between the threading 162 and the filars 144-146 can be facilitated by similarity between the pitch of the filars 144-146 of the coil electrode 130 and the pitch of the internal threading 162. For example, the pitch of the filars 144-146 can be about the same or equal to the pitch of the internal threading 162. The aggregate width of the filars 144-146 arranged in the grouping 156 can be about the same as, or slightly smaller than, the longitudinal distance between adjacent threads of the internal threading 162 (e.g., distance "Y"), such that the filars 144-146 formed in the grouping 156 fit between the threads 162. In some cases, the width of each thread of the internal threading 162 is about the same as, or slightly smaller than, the width of the space 168 between each turn of the grouping 156 (e.g., distance "X").

As shown in FIG. 3, the cable conductor 150 can be pinched between the outer tubular fitting 136 and the floor of the slot 140. The pinching of the cable conductor 150 can mechanically connect the cable conductor 150 to the inner fitting 132 and the outer tubular fitting 136. The pinching can comprise pressure placed on the cable conductor 150 by the outer tubular fitting 136 while the cable conductor 150 is braced against the floor 134 of the slot 140. In some embodiments, the internal threading 162 of the outer tubular fitting 136 directly contacts the cable conductor 150 to apply pressure to the cable conductor 150. In some cases, the cable conductor 150 can be deformed by being pinched between the threading 162 and the floor 134 of the slot 140. The pinching can maintain contact between the cable conductor 150 and one or both of the inner fitting 132 and the outer tubular fitting 136 to support a robust electrical connection between the cable conductor 150, the inner fitting 132, and the outer tubular fitting 136.

In some embodiments, a layer of insulation (not illustrated) can be disposed directly over the cable conductor 150 prior to assembly of the coupling 116. In some cases, the internal threading 162 or other surface that can contact the cable conductor 150 can strip insulation off of the cable conductor 150 during rotational engagement between the inner fitting 132 and the outer tubular fitting 136. The removal of the insulation can facilitate a direct electrical connection between the cable conductor 150 and one or both of the inner fitting 132 and the outer tubular fitting 136.

Figure 4:
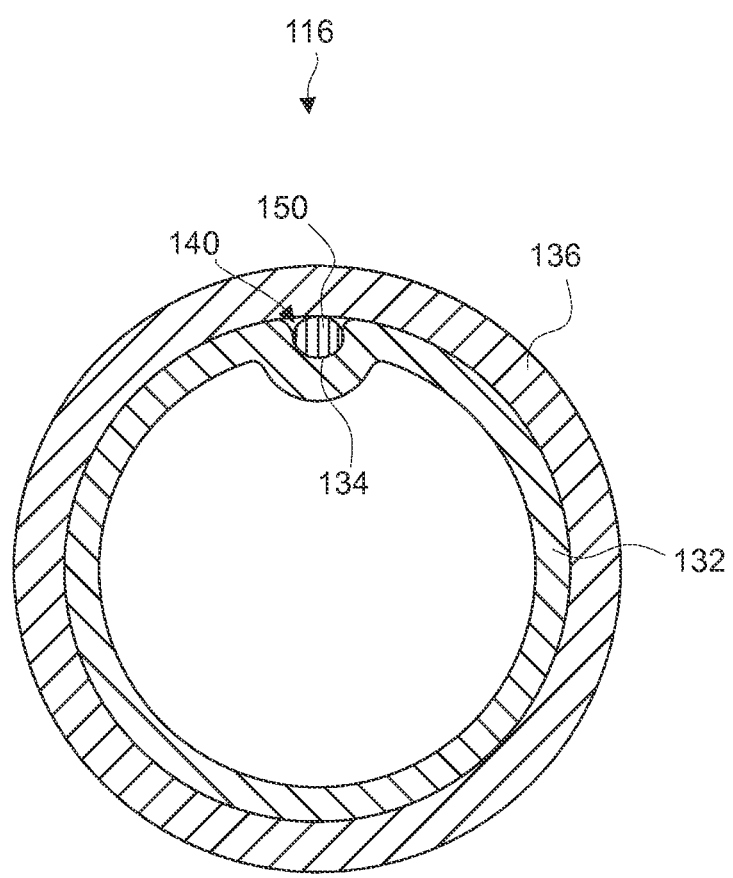
FIG. 4 is a cross-sectional view of an inner fitting within an outer tubular fitting.

FIG. 4 illustrates a cross sectional diagram of the proximal coupling 116. As discussed previously, the cable conductor 150 can have a diameter that is greater than the depth of the slot 140 such that the cable conductor 150 has a bias to protrude out of the slot 140. As shown in FIG. 4, the outer tubular fitting 136 can compress the cable conductor 150 against the floor 134 of the slot 140 such that the cable conductor 150 may not extend above the slot 140. The compression on the cable conductor 150 can elastically or permanently deform the cable conductor 150.

Returning to FIG. 3, the inner fitting 132 can be partially within a polymer tube 138. The inner fitting 132 can be mechanically attached to the polymer tube 138. The polymer tube 138 can be formed by an extrusion process and then placed over the second portion 126 of the inner fitting 132. Heat can then be applied to allow polymer material of the polymer tube 138 (or other polymer component) to integrate into one or more attachment features of the inner fitting 132. As shown in FIG. 2, the attachment feature can be a hole 142. The one or more attachment features can additionally or alternatively comprise one or more projections along the first portion 124 which can be encapsulated by polymer material to support mechanical fixation. In some embodiments, the polymer tube 138 can be attached to the inner fitting 132 by an adhesive. In some embodiments, the polymer tube 138 and/or other component can be formed over the second portion 126 by injection molding.

In some embodiments, the polymer tube 138 can define an exterior surface of the lead body 110. For example, the polymer tube 138 can define an exterior surface of the lead body 110 between the outer tubular fitting 136 and the proximal end 112 of the implantable lead 106. However, in some embodiments, the polymer tube 138 can be relatively shorter. For example, the polymer tube 138 can be joined to another polymer tube (e.g., an extruded tube) that extends along a majority of the length of the tubular body 110. In some embodiments, the polymer tube 138 can have an outer diameter that can be about equal to the outer diameter of the outer tubular fitting 136. The polymer tube 138 and the outer tubular fitting 136 having a similar outer diameter can provide for a relatively smooth exterior surface of the implantable lead 106. It is noted that the larger outer diameter of the second portion 126, relative to the first portion 124, can allow the polymer tube 138 to be placed over the first portion 124 to align with the outer surface of the outer tubular fitting 136 to define a consistent outer diameter of the implantable lead 106.

One or more lumens can extend through the polymer tube 138, the inner fitting 132, the outer tubular fitting 136, and the coil electrode 130. One or more elongated components can extend within the one or more lumens, including one or more conductors (e.g., coil conductors and/or cable conductors), one or more polymer tubes, and/or other components. The one or more conductors can electrically connect the pulse generator 102 to the ring electrode 120 and/or the fixation element 122.

FIG. 3 further illustrates a polymer sleeve 170. The coil electrode 130 can extend within the polymer sleeve 170. The polymer sleeve 170 can be formed by expanded polytetrafluoroethylene (ePTFE), for example. The polymer sleeve 170 can be formed in an extrusion process or a molding process. In some embodiments, the wall of the polymer sleeve is porous such that electrical energy (e.g., a defibrillation shock) can be delivered from the coil electrode 130 through the wall of the polymer sleeve 170 to tissue outside of the polymer sleeve 170. For example, the porous nature of the polymer sleeve 107 can allow bodily fluid to penetrate the wall of the polymer sleeve 170 to support conduction of electrical energy through the wall. In some embodiments, the wall of the polymer sleeve 170 can be formed by conductive material (e.g., a conductive polymer) such that electrical energy can be delivered from the coil electrode 130 through the wall of the polymer sleeve 170 to tissue outside of the polymer sleeve 170. The polymer sleeve 170 can prevent tissue ingrowth into the coil electrode 130, wherein the tissue ingrowth may otherwise unintentionally anchor the implantable lead 106 and/or inhibit the delivery of electrical energy from the coil electrode 130.

The inner diameter of the polymer sleeve 170 can be about equal to the outer diameter of the coil electrode 130. In some embodiments, the inner diameter of the polymer sleeve 170 can be larger than the outer diameter of the coil electrode 130, which can allow the coil electrode 130 to move within the polymer sleeve 170. In some embodiments, the inner diameter of the polymer sleeve 170 can be smaller than the outer diameter of the coil electrode 130 in a relaxed state, wherein the coil electrode 130 can stretch longitudinally to temporarily decrease the outer diameter of the coil electrode 130 to permit the polymer sleeve 170 to be placed over the coil electrode 130.

It is noted that the polymer sleeve 170 can be over the coil electrode 130 before rotational engagement between the coil electrode 130 and the outer tubular fitting 136. As shown in FIG. 3, the wall of the polymer sleeve 170 can be received between the coil electrode 130 and an internal surface of the outer tubular fitting 136. For example, the wall of the polymer sleeve 170 can be compressed between the coil electrode 130 and the internal threading 162. The compression of the wall of the polymer sleeve 170 can mechanically fix the polymer sleeve 170 to the tubular fitting 136. In some embodiments, the polymer sleeve 170 can increase the interference between the internal threading 162 and the filars 144-146 to strengthen the mechanical connection between the coil electrode 130 and the outer tubular fitting 136. In some embodiments, the polymer sleeve 170 can flex relative to the tubular fitting 136 despite being mechanically attached to the tubular fitting 136. In some embodiments, the coil electrode 130 can move within the polymer sleeve 170.

In some embodiments, the polymer sleeve 170 can be shorter than the coil electrode 130, such that some portion of either or both of the proximal end and the distal end of the coil electrode 130 may not be covered by the polymer sleeve 170. In some embodiments, the polymer sleeve 170 can be long enough to extend within both of the proximal coupling 116 and the distal coupling 118 such that the coil electrode 130 is covered by the polymer sleeve 170, the proximal coupling 116 and the distal coupling 118. In some cases, some portion of the proximal end of the coil electrode 132 is not covered by the polymer sleeve 170 such that the filars 144-146 can directly engage the interior surface of the outer tubular fitting 124. It is noted that some embodiments may not include the polymer sleeve 170. As such, the coil electrode 130 may be exposed along the exterior of the implantable lead 106.

Returning to FIG. 2, the window 164 (or other window) can be used to weld the coil electrode 130 to the outer tubular fitting 136 and/or inner fitting 132. In some embodiments, a part of the polymer sleeve 170 can be removed through the window 164 to expose a portion of the coil electrode 130 within the window 164. A welding tool can then weld within the window 164 to electrically and mechanically connect the coil electrode 130 to the tubular fitting 136. Welding of the outer tubular fitting 136 to either or both of the inner fitting 132 and coil electrode 130 can prevent unthreading. In some embodiments, internal threading 162 may not be provided within the outer tubular fitting 136. In such embodiments, a proximal end of the coil electrode 130 can be received within the outer tubular fitting 136 and the coil electrode 130 can be mechanically and electrically attached to the outer tubular fitting 136 by welding the coil electrode 130 to the outer tubular fitting 136 through the window 164.

It is noted that various components can extend within the lead body 110 through the proximal coupling 116 and/or the distal coupling 118. In some embodiments, an elongated polymer member (not illustrated) having one or more lumens containing one or more conductors can extend from the proximal end 112 to the distal end 114 of the implantable lead 106. The elongated polymer member can extend within the lumen 128 of the inner fitting 132 and within the coil electrode 130.

The elongated polymer member can be, for example, a trilumen tube containing one or more cable conductors and/or coil conductors. The one or more conductors within the elongated polymer member can electrically connect to the ring electrode 120 and/or the fixation element 122, for example. In some cases, the cable conductor 150 can extend within a lumen of the elongated polymer member proximally of the proximal coupling 116, extend outside of the elongated polymer member to mechanically and electrically connect with the proximal coupling 116 (e.g., by being pinched within the slot 140), and reenter the lumen of the elongated polymer member distally of the proximal coupling 116. The cable conductor 150 can again extend outside of the elongated polymer member at a location proximal of the distal coupling 118 but distal of the proximal coupling 116 to mechanically and electrically connect with the distal coupling 118.

Figure 5:
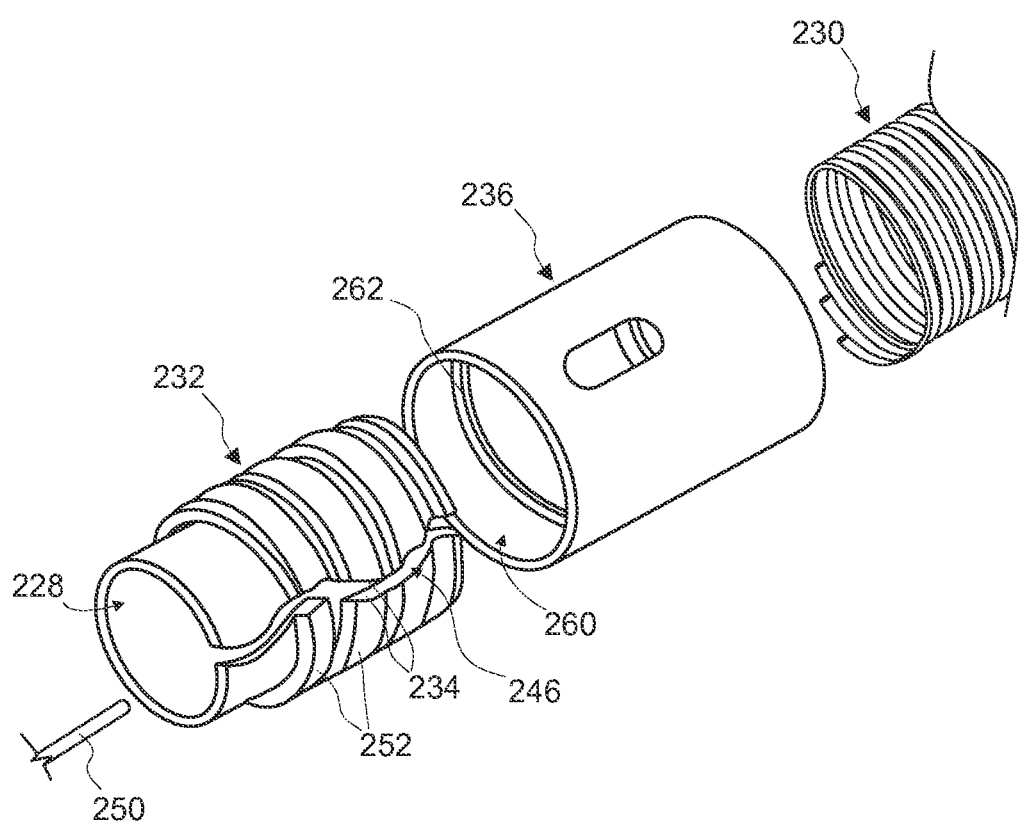
FIG. 5 is an exploded view of a coupling for connecting a cable conductor and a coil electrode.

While various configuration options for the proximal coupling 116 are discussed above, FIG. 5 illustrates another embodiment of the proximal coupling 116. For example, the proximal coupling 116 can comprise an inner fitting 232 and an outer tubular fitting 236. The outer tubular fitting 236 can be structurally similar to the outer tubular fitting 136 as described herein. In some embodiments, the inner fitting 232 can be structurally similar to the inner fitting 132 as described herein except for the configuration of the slot 246. As shown in FIG. 5, the slot 246 can be curved along the length of the inner fitting 232. Alternatively, the slot 246 can be straight and aligned in parallel with the longitudinal axis of the inner fitting 232. As shown in FIG. 5, the slot 246 may not have a floor. For example, the inner fitting 232 can be in a tube configuration and a gap in the wall of the tube can exist along the longitudinal length of the inner fitting 232 to form the slot 246. The gap can be an opening to the lumen of the inner fitting 232 that extends longitudinally along the exterior of the inner fitting 232. The slot 246 can be defined by opposing sides 234 of the wall. The opposing sides 234 can extend along the entire length of the inner fitting 232.

The inner fitting 232 can include a bias shape. For example, the inner fitting 232 can assume a shape having an outer diameter larger than the inner diameter of the lumen 260 of the outer tubular fitting 236. The assumption of the bias shape by the inner fitting 232 can widen the slot 246. The outer diameter of the inner fitting 232 can be reduced when the inner fitting 232 is received within the lumen 260 of the outer tubular fitting 236. The reduction in outer diameter of the inner fitting 232 can narrow the slot 246. Part of the cable conductor 250 can be within the slot 246 while the inner fitting 232 is received within the lumen 260. The cable conductor 250 can be pinched by the opposing walls 234 of the inner fitting 232 as the slot 246 narrows. The pinching of the cable conductor 250 can mechanically connect the cable conductor 250 to the inner fitting 232. Furthermore, the mechanical connection can maintain an electrical connection between the cable conductor 250 and the inner fitting 232.

As discussed previously, a layer of insulation (not illustrated) can be disposed directly over the cable conductor 250. The insulation can be partially removed while the cable conductor 250 is being pinched to facilitate a direct electrical connection between the cable conductor 250 and one or both of the inner fitting 232 and the outer tubular fitting 236. For example, the curved shape of the slot 246 can create one or more pressure points that split, pulverize, strip, or otherwise remove a portion of the insulation to expose the cable conductor 250. As such, the insulation can be removed by the narrowing of the slot 246 as the inner fitting 232 is screwed into the outer tubular fitting 236.

Figure 6:
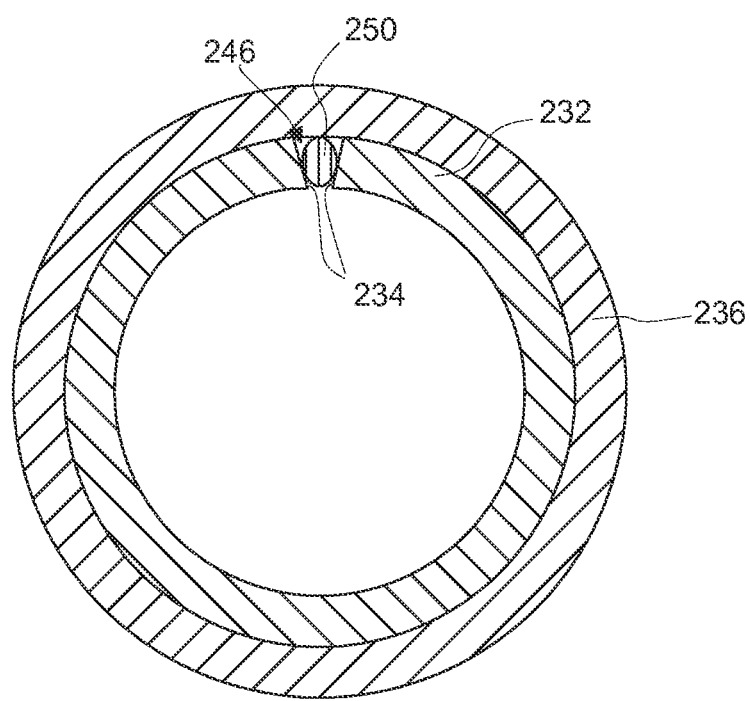
FIG. 6 is a cross-sectional view of an inner fitting within an outer tubular fitting.

FIG. 6 illustrates a cross sectional diagram of the cable conductor 250 pinched within the slot 246 of the inner fitting 232. The cable conductor 250 can be compressed between the opposing sides 234 of the slot 246. In some embodiments, the cable conductor 250 can elastically or permanently deform when the slot 246 is narrowed. The outer tubular fitting 236, by narrowing the slot 246 by constraining the diameter of the inner fitting 232, can maintain the cable conductor 250 in the compressed state.

The distal coupling 118, shown in FIG. 1, can have a similar configuration as the proximal coupling 116 as described and illustrated herein. The distal coupling 118 can be structurally identical to the proximal coupling 116. For example, the distal coupling 118 can include components similar to the polymer tube 138 (extending distally from the distal coupling 118), the inner fitting 132 (or inner fitting 232), and the outer tubular fitting 136 (or outer tubular fitting 236), among other options. A distal end of the coil electrode 130 can be attached to the distal coupling 118 in any manner described herein for connecting the proximal end of the coil electrode 130 to the proximal coupling 116. For example, a distal end of the coil electrode 130, covered by the polymer sleeve 170, can be received within a lumen of an outer tubular fitting and interaction between the filars 144-146 and internal threads of the lumen can fix the coil electrode 130 and the polymer sleeve 170 to the outer tubular fitting of the distal coupling 118. It is noted that the cable conductor 150 is shown as not extending distally of the proximal coupling 116 in FIG. 3. However, in various other embodiments the cable conductor 150 can extend distally of the proximal coupling 116. For example, the cable conductor 150 can be attached to the distal coupling 118 in addition to, or as an alternative to, being attached to the proximal coupling 116.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A method for assembling an implantable lead, the method comprising:
   placing a cable conductor within a slot of an inner fitting, the inner fitting comprising external threading that extends over at least a portion of the inner fitting;
   axially aligning a coil electrode with the inner fitting, the coil electrode having one or more filars, the one or more filars wound in a helical pattern; and
   inserting the coil electrode and the inner fitting into a lumen of an outer tubular sleeve, the lumen having internal threading,
   wherein one or more of the outer tubular fitting, the coil electrode, and the inner fitting are rotated during the insertion such that the internal threading threadably engages both of the one or more filars and the external threading, the cable conductor is pinched within the slot as the inner fitting is inserted into the lumen, and the pinching mechanically connects the cable conductor to the inner fitting.

2. The method of claim 1, wherein axially aligning the coil electrode with the inner fitting comprises aligning the helical pattern of the one or more filars with the external threading to form a continuous thread pattern that overlaps each of the inner fitting and the coil electrode.

3. The method of claim 1, wherein the slot is a gap in a wall of the inner fitting and the insertion of the inner fitting into the lumen narrows the gap to pinch the cable conductor.

4. The method of claim 3, wherein the slot is an indentation in the wall.

5. The method of claim 3, wherein the slot is a gap defined by two opposing sides of the wall, and the cable conductor is pinched by the two opposing sides of the wall by the insertion of the inner fitting into the lumen.

6. The method of claim 1, wherein the slot is relatively wider to receive the cable conductor when the inner fitting is outside of the lumen and the slot is forced to be relatively narrower to pinch the cable conductor by the insertion of the inner fitting into the lumen.

7. The method of claim 1, further comprising welding the inner fitting to the outer tubular fitting when the coil electrode is axially aligned with the inner fitting.

8. The method of claim 1, wherein a layer of insulation covers the cable conductor when the cable conductor is placed within the slot, and a portion of the insulation is removed as the inner fitting is inserted into the lumen of the outer tubular sleeve.

9. The method of claim 8, wherein the portion of the insulation is stripped by the internal threading.

10. The method of claim 1, wherein the helical pattern of the one or more filars and the external threading are aligned to form a continuous thread pattern that overlaps each of the inner fitting and the coil electrode, and the internal threading is threadedly engaged with the continuous thread pattern along each of the inner fitting and the coil electrode.

11. The method of claim 1, wherein upon assembly of the implantable lead, at least part of the outer tubular sleeve defines an exterior surface of the implantable lead.

12. The method of claim 1, wherein each of the inner fitting and the outer tubular fitting are formed from electrically conductive material, and one or both of the inner fitting and the outer tubular fitting electrically connect the cable conductor to the coil electrode upon the insertion of the coil electrode and the inner fitting into the lumen.

13. The method of claim 1, wherein the slot of the outer tubular fitting curves along a longitudinal axis of the outer tubular fitting.

14. A method for assembling an electrode of an implantable lead, the method comprising:
placing a cable conductor within a slot of an inner fitting, the inner fitting comprising external threading that extends over at least a portion of the inner fitting; and
inserting the inner fitting into a lumen of an outer tubular sleeve, the lumen having internal threading,
wherein one or both of the outer tubular fitting and the inner fitting are rotated during the insertion such that the internal threading threadably engages the external threading, the cable conductor is pinched within the slot as the inner fitting is inserted into the lumen, and the pinching mechanically connects the cable conductor to the inner fitting.

15. The method of claim 14, wherein the insertion of the inner fitting into the lumen of the outer tubular sleeve electrically connects the cable conductor to an electrode.

16. The method of claim 15, wherein the outer tubular sleeve comprises at least part of the electrode.

17. The method of claim 15, further comprising connecting the electrode to the outer tubular sleeve.

18. The method of claim 14, wherein the slot is a gap in a wall of the inner fitting and the insertion of the inner fitting into the lumen narrows the gap to pinch the cable conductor.

19. The method of claim 14, wherein upon assembly of the implantable lead, at least part of the outer tubular sleeve defines an exterior surface of the implantable lead.

20. A method for assembling an electrode of an implantable lead, the method comprising:
placing a cable conductor within a slot of a tubular inner fitting; and
inserting the tubular inner fitting into a lumen of an outer tubular sleeve,
wherein the slot is relatively wider to receive the cable conductor when the tubular inner fitting is outside of the lumen and the slot is forced to be relatively narrower to pinch the cable conductor by the insertion of the tubular inner fitting into the lumen to mechanically connect the cable conductor to the tubular inner fitting and electrically connect the cable conductor to the tubular outer fitting.

* * * * *